(12) United States Patent
Nakayama et al.

(10) Patent No.: US 10,463,469 B2
(45) Date of Patent: Nov. 5, 2019

(54) ARTIFICIAL BLOOD VESSEL, METHOD FOR PRODUCING ARTIFICIAL BLOOD VESSEL, AND METHOD FOR PRODUCING POROUS TISSUE REGENERATION SUBSTRATE

(71) Applicant: GUNZE LIMITED, Ayabe-shi, Kyoto (JP)

(72) Inventors: Hidetaka Nakayama, Kyoto (JP); Kosuke Sawai, Shiga (JP); Toshiharu Shinoka, Tokyo (JP); Shuhei Tara, Tokyo (JP); Hirotsugu Kurobe, Tokushima (JP)

(73) Assignee: GUNZE LIMITED, Kyoto (JP)

( * ) Notice: Subject to any disclaimer, the term of this patent is extended or adjusted under 35 U.S.C. 154(b) by 103 days.

(21) Appl. No.: 15/747,815

(22) PCT Filed: Aug. 2, 2016

(86) PCT No.: PCT/JP2016/072626
§ 371 (c)(1),
(2) Date: Jan. 26, 2018

(87) PCT Pub. No.: WO2017/022750
PCT Pub. Date: Feb. 9, 2017

(65) Prior Publication Data
US 2018/0221132 A1    Aug. 9, 2018

(30) Foreign Application Priority Data

Aug. 6, 2015   (JP) .................................. 2015-156204

(51) Int. Cl.
*C08J 9/28* (2006.01)
*A61F 2/06* (2013.01)
(Continued)

(52) U.S. Cl.
CPC .............. *A61F 2/06* (2013.01); *A61L 27/507* (2013.01); *A61L 27/56* (2013.01); *A61L 27/58* (2013.01);
(Continued)

(58) Field of Classification Search
CPC .................. C08J 9/28; C08J 2201/0484; C08J 2201/048; C08J 2201/0522; C08J 2207/10;
(Continued)

(56) References Cited

U.S. PATENT DOCUMENTS

2009/0012607 A1    1/2009 Kim et al.
2010/0278891 A1*  11/2010 Ringeisen .............. A61B 17/80
424/422

(Continued)

FOREIGN PATENT DOCUMENTS

JP    59-501300    7/1984
JP    2001-049018  2/2001
(Continued)

*Primary Examiner* — Paul B Prebilic
(74) *Attorney, Agent, or Firm* — Hamre, Schumann, Mueller & Larson, P.C.

(57) ABSTRACT

The present invention aims to provide a method for producing a porous tissue regeneration substrate that allows a wide choice of solvents and easy adjustment of the bulk density and pore size of the porous substrate. The present invention also aims to provide a method for producing an artificial blood vessel and an artificial blood vessel. The present invention relates a porous, tubular artificial blood vessel containing a bioabsorbable material, the artificial blood vessel including: a skin layer having a relatively small pore size as an innermost layer; and a porous layer positioned around the skin layer and having a relatively large pore size.

5 Claims, 2 Drawing Sheets

(51) Int. Cl.
*A61L 27/50* (2006.01)
*A61L 27/56* (2006.01)
*A61L 27/58* (2006.01)

(52) U.S. Cl.
CPC ......... *C08J 9/28* (2013.01); *C08J 2201/0484* (2013.01); *C08J 2201/0522* (2013.01); *C08J 2205/022* (2013.01); *C08J 2205/024* (2013.01); *C08J 2205/044* (2013.01); *C08J 2207/10* (2013.01); *C08J 2300/16* (2013.01); *C08J 2367/04* (2013.01)

(58) Field of Classification Search
CPC . C08J 2300/16; A61F 2/06; A61F 2210/0004; A61F 2230/0006; A61F 2230/0069; A61F 2240/001; A61L 27/507; A61L 27/56; A61L 27/58; A61L 2430/22; A61L 2430/36
USPC ........................................................ 623/1.39
See application file for complete search history.

(56) References Cited

U.S. PATENT DOCUMENTS

| | | | |
|---|---|---|---|
| 2011/0311746 A1* | 12/2011 | Ma | A61L 27/56 428/36.91 |
| 2012/0058100 A1 | 3/2012 | Shastri et al. | |
| 2014/0311984 A1* | 10/2014 | Nakama | B01J 20/285 210/656 |
| 2018/0221132 A1* | 8/2018 | Nakayama | A61L 27/507 |

FOREIGN PATENT DOCUMENTS

| | | |
|---|---|---|
| JP | 2006-291180 | 10/2006 |
| JP | 2009-011804 | 1/2009 |
| JP | 2010-260952 | 11/2010 |
| JP | 2014-224223 | 12/2014 |
| WO | 84/00302 | 2/1984 |
| WO | 2011153340 | 12/2011 |

* cited by examiner

ARTIFICIAL BLOOD VESSEL, METHOD FOR PRODUCING ARTIFICIAL BLOOD VESSEL, AND METHOD FOR PRODUCING POROUS TISSUE REGENERATION SUBSTRATE

TECHNICAL FIELD

The present invention relates to a method for producing a porous tissue regeneration substrate that allows a wide choice of solvents and easy adjustment of the bulk density and pore size of the porous substrate. The present invention also relates to a method for producing an artificial blood vessel and an artificial blood vessel.

BACKGROUND ART

Recent advances in the cell engineering have enabled culturing of various animal cells, including human cells. Research on the reconstruction of human tissues or organs using such cells, that is, what is called regenerative medicine, is progressing rapidly.

For example, the most frequently used artificial blood vessels in clinic are those containing non-absorbable polymers, such as GORE-TEX. Unfortunately, with the artificial blood vessels containing non-absorbable polymers, anticoagulants and the like have to be continuously administered because the artificial blood vessel remain as a foreign body in the body for a long time after grafting. In addition, when such artificial blood vessels are used in children, repeat surgery is disadvantageously required as they grow older. To overcome the situation, regeneration of blood vessel tissue by regenerative medicine has been attempted.

The point of regenerative medicine is whether cells can grow and differentiate into a three-dimensional, living tissue-like structure. In an exemplary method, a substrate is implanted into the patient's body so that cells from the surrounding tissue or organ can enter the substrate and grow and differentiate to regenerate tissue or an organ.

Porous substrates containing bioabsorbable polymers have been proposed as the substrates for regenerative medicine. With the use of such a porous substrate containing a bioabsorbable polymer as the substrate for regenerative medicine, cells enter the voids in the substrate and grow, leading to rapid regeneration of tissue. In addition, such substrates do not need to be removed by repeat surgery as they are decomposed and absorbed in the living body after certain periods of time.

With regard to methods for producing the porous substrates containing bioabsorbable polymers, Patent Literature 1, for example, discloses a method for producing a porous substrate by adding water-soluble particles such as sodium chloride or saccharide particles to a bioabsorbable polymer solution, freeze-drying the resulting solution, and then leaching out and removing the particles by washing with water.

Unfortunately, in the method disclosed in Patent Literature 1, dispersing the particles in the bioabsorbable polymer solution is difficult, so that precipitation of the particles causes the resulting porous substrate to have a non-uniform pore size distribution. In addition, complete removal of the particles requires a complicated process. Furthermore, disadvantageously, it is substantially impossible to produce a porous substrate when the bioabsorbable polymer solution has high viscosity.

To overcome the situation, methods for producing a porous substrate by a phase separation process have been proposed. These methods include mixing good and poor solvents for a bioabsorbable polymer so as to form a uniform phase, followed by cooling to give a porous body. For example, Patent Literature 2 discloses a method for producing a porous substrate including dissolving a polymer containing a lactide-caprolactone copolymer into a mixed solution of good and poor solvents for the polymer, followed by cooling. Patent Literature 3 discloses a method for producing a porous substrate including adding polylactic acid to a mixed solution containing an organic solvent capable of dissolving the polylactic acid, an organic solvent not dissolving the polylactic acid, and water, followed by heating at 40° C. to 100° C. to dissolve the polylactic acid, and further followed by cooling.

In the porous substrates containing bioabsorbable polymers, control of properties such as pore size and bulk density is extremely important from the standpoint of mechanical strength to serve as a tissue regeneration scaffold, bioabsorption behavior, permeability to cells, supply of nutrition to cells entering the substrate, and the like. In the phase separation process, the pore size of the resulting porous substrate can be adjusted by adjustment of the mixing ratio between the good solvent and the poor solvent. However, the adjustment of the pore size of the porous substrate in this manner greatly varies the bulk density of the resulting porous substrate. Specifically, for a porous substrate with a large pore size, the ratio of the poor solvent has to be high. This makes the ratio of the good solvent relatively low, so that the resulting porous substrate has a small bulk density. Conversely, for a porous substrate with a small pore size, the ratio of the good solvent is set high and that of the poor solvent set low, so that the resulting porous substrate has a large bulk density. Therefore, unfortunately, a porous substrate having a different pore size but the same bulk density is very difficult to produce by the phase separation process. Furthermore, the phase separation process requires that the good solvent and the poor solvent are compatible with each other. When water, which is easy to handle, is selected as the poor solvent, there are only limited choices of good solvents such as 1,4-dioxane, N-methylpyrrolidone, and dimethyl sulfoxide. These solvents are highly toxic to the living body, and thus steps for completely removing the solvents from the porous substrates are required for clinical application. This disadvantageously makes the production process complicated.

CITATION LIST

Patent Literature

Patent Literature 1: JP 2001-49018 A
Patent Literature 2: JP 2006-291180 A
Patent Literature 3: JP 2010-260952 A

SUMMARY OF INVENTION

Technical Problem

In view of the situation in the art, the present invention aims to provide a method for producing a porous tissue regeneration substrate that allows a wide choice of solvents and easy adjustment of the bulk density and pore size of the porous substrate. The present invention also aims to provide a method for producing an artificial blood vessel and an artificial blood vessel.

Solution to Problem

The present invention includes a method for producing a porous tissue regeneration substrate containing a bioabsorbable polymer, the method including: a dissolving step of preparing a uniform solution containing a bioabsorbable polymer dissolved therein using a bioabsorbable polymer, a solvent 1 having a relatively low solvency for the bioabsorbable polymer, a solvent 2 having a relatively high solvency for the bioabsorbable polymer and being incompatible with the solvent 1, and a common solvent 3 compatible with the solvent 1 and the solvent 2; a precipitating step of cooling the uniform solution to precipitate a porous body containing the bioabsorbable polymer; and a freeze-drying step of freeze-drying the porous body containing the bioabsorbable polymer to give a porous tissue regeneration substrate.

The present invention will be described in detail below.

The present inventors devised a method for producing a porous tissue regeneration substrate in which good and poor solvents for a bioabsorbable polymer are used in combination with a common solvent compatible with both of the good and poor solvents. With the common solvent, the good solvent and the poor solvent do not have to be compatible with each other. This allows a much wider choice of combinations of good solvents and poor solvents. In the method for producing a porous tissue regeneration substrate of the present invention, the good solvent can be a less toxic organic solvent other than 1,4-dioxane, N-methylpyrrolidone, or dimethyl sulfoxide. Furthermore, the bulk density and pore size of the porous substrate can be easily adjusted by combining two or more common solvents and adjusting the mixing ratio between the two or more common solvents.

In the method for producing a porous tissue regeneration substrate of the present invention, first, a dissolving step is performed. In this step, a uniform solution containing a bioabsorbable polymer dissolved therein is prepared using a bioabsorbable polymer, a solvent 1, a solvent 2, and a common solvent 3.

Examples of the bioabsorbable polymer include synthetic polymers such as polyglycolide, polylactide, poly-ε-caprolactone, lactide-glycolic acid copolymer, glycolide-ε-caprolactone copolymer, lactide-ε-caprolactone copolymer, polycitric acid, polymalic acid, poly-α-cyanoacrylate, poly-β-hydroxy acid, polytrimethylene oxalate, polytetramethylene oxalate, polyorthoester, polyorthocarbonate, polyethylene carbonate, poly-γ-benzyl-L-glutamate, poly-γ-methyl-L-glutamate, poly-L-alanine, polyglycol, and sebacic acid, polysaccharides such as starch, alginic acid, hyaluronic acid, chitin, pectic acid, and derivatives thereof, and natural polymers such as proteins (e.g., gelatin, collagen, albumin, fibrin). These bioabsorbable materials may be used alone or in combination of two or more thereof.

The solvent 1 is a solvent having a relatively low solvency for the bioabsorbable polymer, i.e., what is called a poor solvent. The phrase "having a relatively low solvency" as used herein means that the solvent is less likely to dissolve the bioabsorbable polymer than the solvent 2 is.

When the bioabsorbable polymer is a synthetic polymer, the solvent 1 may be water, methanol, n-propanol, isopropanol, or n-butanol, for example. In particular, water is suitable because of its excellent handleability.

The solvent 2 is a solvent having a relatively high solvency for the bioabsorbable polymer, i.e., what is called a good solvent.

The solvent 2 is incompatible with the solvent 1. The "incompatible" as used herein means phase separation occurs even after mixing and stirring at a room temperature of 25° C.

In cases where the bioabsorbable polymer is a synthetic polymer and water is selected as the solvent 1, the solvent 2 may be an organic solvent such as methyl ethyl ketone, diethyl ketone, methyl propyl ketone, methyl isobutyl ketone, methylamino ketone, cyclohexanone, chloroform, ethyl acetate, or toluene. In particular, for example, methyl ethyl ketone and chloroform are suitable because they have relatively low toxicity.

The common solvent 3 is compatible with both of the solvent 1 and the solvent 2. Combining such a common solvent 3 with the solvent 1 and the solvent 2 enables production of a porous tissue regeneration substrate by a phase separation process even if the solvent 1 and the solvent 2 are incompatible with each other. This remarkably widens the choice of combinations of the solvents 1 and 2. The "compatible" as used herein means phase separation does not occur even after mixing and stirring at a room temperature of 25° C.

In cases where the bioabsorbable polymer is a synthetic polymer, water is selected as the solvent 1, and an organic solvent is selected as the solvent 2, the common solvent 3 may be, for example, acetone, methanol, ethanol, propanol, isopropanol, n-butanol, 2-butanol, isobutanol, or tetrahydrofuran.

The mixing ratio between the solvent 1 and the solvent 2 is not limited. Preferably, the weight ratio between the solvent 1 and the solvent 2 is within the range of 1:1 to 1:100. With the weight ratio within this range, a uniform porous tissue regeneration substrate can be produced. The weight ratio is more preferably within the range of 1:10 to 1:50.

The mixing ratio between the total of the solvent 1 and the solvent 2 and the common solvent 3 is not limited. Preferably, the weight ratio between the total of the solvent 1 and the solvent 2 and the common solvent 3 is within the range of 1:0.01 to 1:0.5. With the weight ratio within this range, a uniform porous tissue regeneration substrate can be produced. The weight ratio is more preferably within the range of 1:0.02 to 1:0.3.

The pore size of the resulting porous tissue regeneration substrate can be controlled by adjusting the mixing ratio between the solvent 1 and the solvent 2. Specifically, an increase in the ratio of the solvent 1 increases the pore size of the resulting porous tissue regeneration substrate, and an increase in the ratio of the solvent 2 decreases the pore size of the resulting porous tissue regeneration substrate. However, the control of the pore size by the method of adjusting the mixing ratio between the solvent 1 and the solvent 2 unfortunately varies the bulk density at the same time. It is thus difficult to produce a porous tissue regeneration substrate having desired pore size and bulk density by this method.

Thus, in the method for producing a porous tissue regeneration substrate of the present invention, preferably, two or more common solvents 3 are used in combination (hereinafter, the two or more solvents included in the common solvent 3 are referred to as a "common solvent 3-1", a "common solvent 3-2", . . . ). The pore size of the resulting porous tissue regeneration substrate can be controlled by combining two or more common solvents 3, for example, a common solvent 3-1 and a common solvent 3-2, and adjusting the mixing ratio between these solvents. In other words, the pore size of the resulting porous body can be controlled by adjusting the mixing ratio between the common solvent 3-1 and the common solvent 3-2 included in the common solvent 3 while holding the mixing ratio between the solvent 1, the solvent 2, and the common solvent 3 constant. This means that the bulk density of the resulting porous tissue regeneration substrate can remain substantially constant while only the pore size is adjusted. This method for producing a porous tissue regeneration substrate of the present invention makes it easy to produce a porous tissue regeneration substrate having desired pore size and bulk density.

The combination of the bioabsorbable polymer and the solvents is not limited. Examples of the combination include: a combination of a lactide-ε-caprolactone copolymer as the bioabsorbable polymer with water as the solvent 1, methyl ethyl ketone as the solvent 2, acetone as the common solvent 3-1, and ethanol as the common solvent 3-2; a combination of polylactide as the bioabsorbable polymer with water as the solvent 1, chloroform as the solvent 2, tetrahydrofuran as the common solvent 3-1, and ethanol as the common solvent 3-2; and a combination of polylactide as the bioabsorbable polymer with water as the solvent 1, chloroform as the solvent 2, acetone as the common solvent 3-1, and ethanol as the common solvent 3-2.

In the dissolving step, a uniform solution containing a bioabsorbable polymer dissolved therein is prepared using the bioabsorbable polymer, the solvent 1, the solvent 2, and the common solvent 3.

More specifically, for example, the uniform solution may be prepared by a method involving mixing the bioabsorbable polymer with a mixed solvent containing the solvent 1, solvent 2, and common solvent 3 (hereinafter also referred to simply as "mixed solvent"), followed by heating. Simpler methods for preparing the uniform solution include a method involving heating the mixed solvent in advance and adding the bioabsorbable polymer to the heated mixed solvent; and a method involving dissolving the bioabsorbable polymer into the solvent 2 and then adding the solvent 1 and the common solvent 3 with heating.

The mixing method is not limited. For example, a known mixing method using stirrer chips or stirring bars may be used.

The heating temperature in the dissolving step may be any temperature at which the bioabsorbable polymer is uniformly dissolved. Preferably, the heating temperature is lower than the boiling point of any of the solvent 1, the solvent 2, and the common solvent 3. Heating to the boiling point or higher may vary the mixing ratio between the solvents, which may make it impossible to control the pore size and bulk density of the resulting porous tissue regeneration substrate.

In the method for producing a porous tissue regeneration substrate of the present invention, next, a precipitating step is performed. In this step, the uniform solution is cooled to precipitate a porous body containing the bioabsorbable polymer. Cooling the uniform solution precipitates a porous body containing the bioabsorbable polymer that has become insoluble. This is presumably because, before the bioabsorbable polymer crystallizes and precipitates, phase separation (liquid-liquid phase separation) of the bioabsorbable polymer in the liquid state and the solvents occurs due to thermodynamic instability at a temperature higher than the temperature at which the bioabsorbable polymer crystallizes.

The cooling temperature in the precipitating step may be any temperature at which the porous body containing the bioabsorbable polymer can precipitate. Preferably, the temperature is 4° C. or lower, more preferably −24° C. or lower.

The cooling rate also affects the pore size of the resulting porous tissue regeneration substrate. Specifically, a higher cooling rate tends to result in a smaller pore size, and a slower cooling rate tends to result in a larger pore size. Thus, especially for production of a porous tissue regeneration substrate with a small pore size, the cooling temperature may be set low and the uniform solution may be cooled rapidly.

In the method for producing a porous tissue regeneration substrate of the present invention, next, a freeze-drying step is performed. In this step, the obtained porous body containing the bioabsorbable polymer is freeze-dried to give a porous tissue regeneration substrate. The freeze-drying may be performed under any conditions, and may be performed under conventionally known conditions.

The freeze-drying step may be performed after the cooling step without any further treatment; however, for removal of the organic solvents used as the solvents, the porous body may be immersed in ethanol, water, and the like to replace the organic solvents before freeze-drying.

The method for producing a porous tissue regeneration substrate of the present invention enables production of a porous tissue regeneration substrate with easy adjustment of the bulk density and the pore size and without the use of highly toxic solvents.

The resulting porous tissue regeneration substrate can be especially suitably used for regeneration of blood vessels, neurons, and the like.

In particular, a tubular artificial blood vessel produced by the method for producing a porous tissue regeneration substrate of the present invention can exhibit very superior performance.

In the following, the production of an artificial blood vessel by the method for producing a porous tissue regeneration substrate of the present invention will be described in more detail.

The method for producing a tubular artificial blood vessel includes a dissolving step, a precipitating step, and a freeze-drying step performed in the stated order, as the method for producing a porous tissue regeneration substrate of the present invention, and includes a step for forming the porous body into a tubular shape after the dissolving step and before the precipitating step.

Specifically, an application step of applying the uniform solution obtained in the dissolving step to a surface of a rod-shaped body is performed. Thereafter, the precipitating step is performed. In the precipitating step, the uniform solution on the surface of the rod-shaped body is cooled to precipitate a tubular porous body containing the bioabsorbable polymer around the rod-shaped body.

The rod-shaped body is a member used for forming the porous body into a tubular shape. The diameter of the rod-shaped body substantially corresponds to the inner diameter of the tubular artificial blood vessel obtained when the rod-shaped body is pulled out from the obtained porous body.

The present inventors found out that especially in cases where the rod-shaped body is a rod-shaped body containing a metal such as stainless steel or resin-coated stainless steel, the resulting tubular artificial blood vessel allows, when grafted, regeneration of a quite normal blood vessel less susceptible to hypertrophy and calcification.

The reason for this is presumably as follows. In the precipitating step of cooling the uniform solution on the surface of the rod-shaped body to precipitate a porous body containing the bioabsorbable polymer around the rod-shaped body, the inner portion of the tube in contact with the rod-shaped body containing a highly thermally conductive metal is rapidly cooled, thus forming a layer (hereinafter, also referred to as a "skin layer") having a relatively small pore size as compared with the surrounding portion (hereinafter, also referred to as a "porous layer"). For blood vessel regeneration, the artificial blood vessel as a whole needs to have pores with a pore size sufficient for entrance of cells. On the inner portion, which directly contacts blood flow, however, it is important to prevent deposition of platelets, a cause of hypertrophy and calcification. The formation of the skin layer on the inner side of the tubular artificial blood vessel prevents the deposition of platelets on the inner portion that contacts with blood flow, while allowing easy entrance of cells in other portions. This presumably leads to the regeneration of a quite normal blood vessel.

Figure 4:
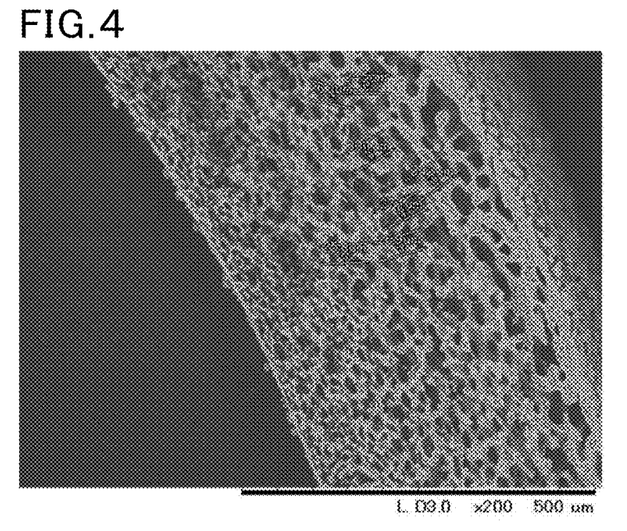
FIG. 4 shows an electron micrograph of a cross section of an artificial blood vessel in which a skin layer is on the inner side and the pore size of a porous layer around the skin layer increases outward.

It is also possible, by adjusting the type of the rod-shaped body, the method for cooling the rod-shaped body, and the like, to produce an artificial blood vessel in which the skin layer is on the inner side and the pore size of the porous layer around the skin layer increases outward. (FIG. 4 shows an electron micrograph of a cross section of a tubular artificial blood vessel with such a structure). Conversely, it is also possible to produce an artificial blood vessel in which the skin layer is on the outer side and the pore size of the porous layer inside the skin layer increases inward.

The uniform solution may be applied to the surface of the rod-shaped body by any method. Examples of the method include a method involving dipping the rod-shaped body into the uniform solution one or two or more times; and a method involving placing the rod-shaped body in a tubular body having an inner diameter larger than the diameter of the rod-shaped body and pouring the uniform solution into the gap between the rod-shaped body and the tubular body.

Since the resulting tubular porous body slightly shrinks in the precipitating step, the rod-shaped body and the tubular body are easily pulled out; however, the surface of the rod-shaped body and the tubular body may be subjected to smoothing treatment such as coating in advance.

The present invention also includes a method for producing a porous, tubular artificial blood vessel containing a bioabsorbable material, the method including: a dissolving step of preparing a uniform solution containing a bioabsorbable polymer dissolved therein using a bioabsorbable polymer, a solvent 1 having a relatively low solvency for the bioabsorbable polymer, a solvent 2 having a relatively high solvency for the bioabsorbable polymer and being incompatible with the solvent 1, and a common solvent 3 compatible with the solvent 1 and the solvent 2; an applying step of applying the uniform solution to a surface of a rod-shaped body; a precipitating step of cooling the uniform solution on the surface of the rod-shaped body to precipitate a tubular porous body containing the bioabsorbable polymer around the rod-shaped body; and a freeze-drying step of freeze-drying the tubular porous body to give a tubular artificial blood vessel.

The present invention also includes a porous, tubular artificial blood vessel containing a bioabsorbable material, the artificial blood vessel including: a skin layer having a relatively small pore size as an innermost layer; and a porous layer positioned around the skin layer and having a relatively large pore size.

A quite normal blood vessel less susceptible to hypertrophy and calcification can be regenerated by grafting the artificial blood vessel of the present invention.

The inner diameter of the artificial blood vessel of the present invention is not limited. From the standpoint of the inner diameter of typical blood vessels, the lower limit of the inner diameter is preferably 0.5 mm, and the upper limit thereof is preferably about 8.0 mm. The outer diameter of the artificial blood vessel is not limited. From the standpoint of the outer diameter of typical blood vessels, the lower limit of the outer diameter is preferably 1.0 mm, and the upper limit thereof is preferably about 10.0 mm.

Artificial blood vessels usable for peripheral blood vessels having an inner diameter of about 2.0 to 5.0 mm are particularly difficult to produce by conventional methods. Such artificial blood vessels, however, can be easily produced by the method for producing an artificial blood vessel of the present invention.

Figure 1:
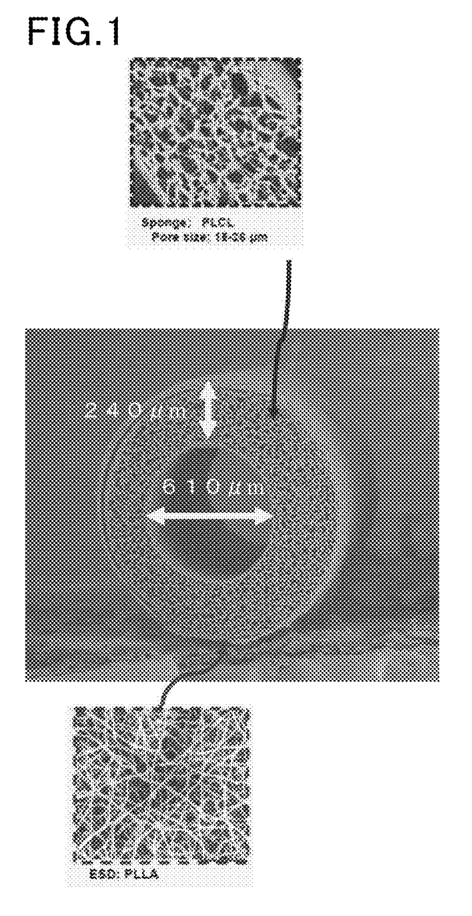
FIG. 1 shows electron micrographs of a cross section of a tubular artificial blood vessel obtained in Experiment Example 4.

The skin layer means a layer containing a large number of fine pores or holes inside and positioned near the surface of the innermost portion of the artificial blood vessel of the present invention, the layer having, in a cross section of the artificial blood vessel of the present invention, a relatively small average pore size (e.g., about 1 μm) as compared with the average pore size (e.g., about 25 μm) in the vicinity of the middle portion of the cross section as in FIG. 4 or FIG. 1, which shows electron micrographs of a cross section of a tubular artificial blood vessel obtained in Experiment Example 4 (described later), for example.

The function of the skin layer is not necessarily clear. However, for example, forming an artificial blood vessel with nano-fibers and enhancing its surface smoothness have been found in vitro to tend to reduce the deposition of platelets that cause blood clots (Acta Biomaterialia 8 (2012) 4349-4356). Additionally, a polymer surface with a small pore size has been found in vitro to have an improved surface contact angle because of the lotus effect and thus reduce the deposition of platelets that cause blood clots (Colloids Surf B Biointerfaces 2014 Feb. 1; 114: 28-35). In view of these findings, the presence of the skin layer as the innermost layer of the artificial blood vessel of the present invention presumably improves the smoothness of the inner surface as well as reduces excessive blood clot formation by the lotus effect. This presumably facilitates the formation of the intima, which makes the blood vessel less susceptible to hypertrophy and calcification.

The lower limit of the pore size of the pores constituting the pore structure of the skin layer is preferably 0.5 μm, and the upper limit thereof is preferably 20 μm. With the pore size of the pores constituting the pore structure of skin layer within this range, the prevention effect on hypertrophy and calcification is particularly exhibited. The lower limit of the pore size of the pores constituting the pore structure of the skin layer is more preferably 1 μm, and the upper limit thereof is more preferably 18 μm. The lower limit is still more preferably 3 μm, and the upper limit is still more preferably 15 μm.

Although the boundary between the skin layer and the porous layer is not always clear, the lower limit of the thickness of the skin layer is preferably 0.1 μm, and the upper limit thereof is preferably 30 μm. With the thickness of the skin layer within this range, a quite normal blood vessel less susceptible to hypertrophy and calcification can be regenerated. If the thickness of the skin layer is smaller than 0.1 μm, it may be difficult to uniformly form a porous layer having a relatively large pore size around the skin layer. If the thickness of the skin layer is larger than 30 μm, permeability to cells may be poor, which may results in a delay in tissue regeneration. The lower limit of the thickness of the skin layer is more preferably 0.5 μm, and the upper limit thereof is more preferably 20 μm.

The porous layer means a layer other than the skin layer that includes, in a cross section of the artificial blood vessel of the present invention, the vicinity of the middle portion (in which the average pore size is about 25 μm, for example) of the cross section as in FIG. 4 or FIG. 1, which shows electron micrographs of a cross section of a tubular artificial blood vessel obtained in Experiment Example 4 (described later), for example.

The pore structure of the porous layer is far less dense than that of the skin layer, and the pore structure communicates with the skin layer. The pore structure more preferably has open pores (open voids) of a uniform size, particularly preferably has open pores (open voids) of a uniform size and also has at least one pore or hole in the pore walls themselves.

The lower limit of the pore size of the pores constituting the pore structure of the porous layer is preferably 1 μm, and the upper limit thereof is preferably 500 μm. If the pore size of the pores constituting the pore structure of the porous layer is smaller than 1 μm, permeability to cells may be poor. If the pore size is larger than 500 μm, good permeability to cells is obtained, but some cells pass through the artificial blood vessel and escape therefrom, which may result in a delay in tissue regeneration. The lower limit of the pore size of the pores constituting the pore structure of the porous layer is more preferably 5 μm, and the upper limit thereof is more preferably 400 μm. The lower limit is still more preferably 10 μm, and the upper limit is still more preferably 300 μm.

The at least one pore or hole in the pore walls themselves in the porous layer preferably has a maximum diameter that is equal to or smaller than the pore size of the pores constituting the pore structure of the porous layer. The upper limit of the maximum diameter of the at least one pore or hole in the pore walls themselves in the porous layer is preferably 500 μm, more preferably 400 μm, still more preferably 300 μm.

The artificial blood vessel of the present invention preferably has, on the porous layer, an ultrafine fiber nonwoven fabric layer containing a bioabsorbable polymer and containing ultrafine fibers with a fiber size of 10 to 5,000 nm. Formation of such an ultrafine fiber nonwoven fabric layer prevents leakage of blood due to blood flow pressure. The ultrafine fiber nonwoven fabric layer also exhibits sufficient strength against external pressure after grafting and thus can prevent blockage of the blood vessel due to kinking.

The ultrafine fiber nonwoven fabric layer may contain any bioabsorbable polymer. For example, any of the above synthetic polymers, natural polymers, and the like may be used.

In particular, preferably, two or more bioabsorbable polymers different in bioabsorbability are used in combination as the bioabsorbable polymer constituting the ultrafine fiber nonwoven fabric layer. Although the ultrafine fiber nonwoven fabric layer improves the strength of the artificial blood vessel, it can prevent the entrance of the cells and thereby delay blood vessel regeneration or cause calcification. This can be remarkably improved by combining two bioabsorbable polymers different in bioabsorbability to constitute the ultrafine fiber nonwoven fabric layer.

For example, polyglycolide with a relatively high bioabsorbability and polylactide with a relatively low bioabsorbability may be combined to constitute the ultrafine fiber nonwoven fabric layer. In this case, neither of the two bioabsorbable polymers decomposes in the relatively early period just after grafting when strength is particularly required, so that a high strength-improving effect can be exhibited. Thereafter, voids are formed in the ultrafine fiber nonwoven fabric layer as the polyglycolide with a relatively high bioabsorbability is gradually decomposed and absorbed. These voids allow easy entrance of cells, leading to promotion of blood vessel regeneration and prevention of calcification.

The lower limit of the thickness of the ultrafine fiber nonwoven fabric layer is preferably 10 μm, and the upper limit thereof is preferably 300 μm. With the thickness of the ultrafine fiber nonwoven fabric layer within this range, a sufficient strength-improving effect can be obtained.

The ultrafine fiber nonwoven fabric layer may be formed on the porous layer by any method, but preferably formed by electrospinning. Electrospinning is a method involving discharging a solution containing a bioabsorbable polymer dissolved therein to the target from a nozzle while applying high voltage between the nozzle and a collector electrode. The solution ejected from the nozzle is formed into the shape of ultrafine fibers along the lines of electric force, and deposits onto the target.

In the method for producing an artificial blood vessel of the present invention, when a conductive rod-shaped body containing a metal is used as the rod-shaped body, the rod-shaped body can be used as the collector electrode. In this case, the ultrafine fiber nonwoven fabric layer can be formed by discharging the solution while rotating the rod-shaped body with the tubular artificial blood vessel therearound and reciprocating the nozzle multiple times.

The artificial blood vessel of the present invention may further contain an agent that prevents blood clot formation, such as heparin, and a growth factor that promotes blood vessel regeneration, such as bFGF. Cells such as mesenchymal stem cells may be seeded onto the artificial blood vessel prior to implantation.

Advantageous Effects of Invention

The present invention provides a method for producing a porous tissue regeneration substrate that allows a wide choice of solvents and easy adjustment of the bulk density and pore size of the porous substrate. The present invention also provides a method for producing an artificial blood vessel and an artificial blood vessel.

DESCRIPTION OF EMBODIMENTS

The embodiments of the present invention will be described in more detail with reference to examples. The present invention however is not limited to these examples.

EXPERIMENT EXAMPLE 1

(1) Production of Porous Tissue Regeneration Substrate

At a room temperature of 25° C., 0.25 g of a L-lactide-ε-caprolactone copolymer (molar ratio: 50:50) was mixed with a mixed solution containing 0.3 mL of water as the solvent 1, 2.0 mL of methyl ethyl ketone as the solvent 2, 1.0 mL of a mixture of acetone (common solvent 3-1) and ethanol (common solvent 3-2) as the common solvent 3. Thus, a non-uniform solution not dissolving the L-lactide-ε-caprolactone copolymer was obtained.

Subsequently, the obtained non-uniform solution was put in a glass tube with a diameter of 3.3 mm and heated at 60° C. to give a uniform solution containing the L-lactide-ε-caprolactone copolymer dissolved therein.

The obtained uniform solution was then cooled to 4° C. or −24° C. in a freezer to precipitate a porous body containing the L-lactide-ε-caprolactone copolymer.

The obtained porous body was immersed in an ethanol bath (50 mL) at 4° C. or −24° C. for 12 hours, and then immersed in a water bath (50 mL) at 25° C. for 12 hours for washing.

Thereafter, the porous body was freeze-dried at −40° C. to give a cylindrical porous tissue regeneration substrate with a diameter of 3.0 mm and a height of 15 mm.

Porous tissue regeneration substrates were produced at two different ratios between the common solvent 3-1 and the common solvent 3-2, 0.8:0.2 and 0.5:0.5.

(2) Measurement of Pore Size and Bulk Density of Porous Substrate

The pore size and bulk density of the obtained porous substrates were measured by the following method.

Table 1 shows the results.

(2-1) Measurement of Pore Size

The cylindrical porous tissue regeneration substrate was cut, and an electron micrograph in the vicinity of the middle of the obtained cross section was taken at 1,000- or 8,000-fold magnification. The pore diameter (major axis) was measured at random 10 sites in the obtained electron microscopic image and the average was taken as the average pore size.

(2-2) Measurement of Bulk Density

The volume and weight of the obtained blood vessel substrate was measured. The mass was divided by the volume to determine the bulk density. Three measurements were performed for each substrate, and the average was taken as the bulk density.

TABLE 1

| | | Common solvent 3-1:Common solvent 3-2 | |
| --- | --- | --- | --- |
| | | 0.8:0.2 | 0.5:0.5 |
| Cooling temperature 4° C. | Average pore size (μm) | 16.5 | 10.5 |
| | Bulk density (kg/m$^3$) | 170 | 180 |
| Cooling temperature −24° C. | Average pore size (μm) | 80.6 | 5.54 |
| | Bulk density (kg/m$^3$) | 250 | 230 |

EXPERIMENT EXAMPLE 2

At a room temperature of 25° C., 0.5 g of polylactide was mixed with a mixed solution containing 0.15 mL of water as the solvent 1, 6.0 mL of chloroform as the solvent 2, and 1.0 mL of a mixture of tetrahydrofuran (common solvent 3-1) and ethanol (common solvent 3-2) as the common solvent 3 while heating at 60° C. Thus, a uniform solution containing the polylactide dissolved therein was obtained.

Subsequently, the obtained uniform solution was cooled to −80° C. in a freezer to precipitate a porous body containing the polylactide.

The obtained porous body was immersed in an ethanol bath (50 mL) at −70° C. for 12 hours, and then immersed in a water bath (50 mL) at 25° C. for 12 hours for washing.

The porous body was then freeze-dried at −40° C. to give a porous tissue regeneration substrate.

Porous tissue regeneration substrates were produced at two different ratios between the common solvent 3-1 and the common solvent 3-2, 0.9:0.1 and 0.1:0.9.

The pore size and bulk density of the obtained porous substrates were measured in the same manner as in Experiment Example 1.

Table 2 shows the results.

TABLE 2

| | Common solvent 3-1:Common solvent 3-2 | |
| --- | --- | --- |
| | 0.9:0.1 | 0.1:0.9 |
| Average pore size (μm) | 0.86 | 1.80 |
| Bulk density (kg/m$^3$) | 229 | 236 |

EXPERIMENT EXAMPLE 3

While heating at 60° C., 0.5 g of polylactide was dissolved in chloroform as the solvent 2. Subsequently, while continuing heating, acetone (common solvent 3-1) and then ethanol (common solvent 3-2) as the common solvent 3 were added in a total amount of 2.8 mL. Further, 0.22 mL of water as the solvent 1 was added, thus a uniform solution was obtained. The obtained uniform solution was cooled to −80° C. in a freezer to precipitate a porous body containing the polylactide.

The obtained porous body was immersed in an ethanol bath (50 mL) at −70° C. for 12 hours, and then immersed in a water bath (50 mL) at 25° C. for 12 hours for washing.

Thereafter, the porous body was freeze-dried at −40° C. to give a porous tissue regeneration substrate.

Porous tissue regeneration substrates were produced at two different ratios between the common solvent 3-1 and the common solvent 3-2, 1.8:1.0 and 1.0:1.8.

The pore size and bulk density of the obtained porous substrates were measured in the same manner as in Experiment Example 1.

Table 3 shows the results.

TABLE 3

| | Common solvent 3-1:Common solvent 3-2 | |
| --- | --- | --- |
| | 1.8:1.0 | 1.0:1.8 |
| Average pore size (μm) | 9.8 | 65.2 |
| Bulk density (kg/m$^3$) | 177 | 166 |

EXPERIMENT EXAMPLE 4

(1) Production of Artificial Blood Vessel

At a room temperature of 25° C., 0.25 g of an L-lactide-ε-caprolactone copolymer (molar ratio: 50:50) was mixed with a mixed solution containing 0.2 mL of water as the solvent 1, 2.5 mL of methyl ethyl ketone as the solvent 2, and 0.8 mL of acetone and 0.2 mL of ethanol as the common solvent 3. Thus, a non-uniform solution not dissolving the L-lactide-ε-caprolactone copolymer was obtained.

Subsequently, the obtained non-uniform solution was heated at 60° C. to give a uniform solution containing the L-lactide-ε-caprolactone copolymer dissolved therein.

A fluorine-coated stainless steel rod-shaped body with a diameter of 0.6 mm was placed in a glass tube with an inner diameter of 1.1 mm. The uniform solution was poured into the gap between the rod-shaped body and the glass tube. The uniform solution in this state was cooled to −30° C. in a freezer to precipitate a porous body containing the L-lactide-ε-caprolactone copolymer around the rod-shaped body. The obtained porous body was immersed in an ethanol bath (50 mL) at −30° C. for 12 hours, and then immersed in a water bath (50 mL) at 25° C. for 12 hours for washing.

Thereafter, the porous body was freeze-dried at −40° C. to give a tubular porous body.

Polyglycolide and polylactide were separately dissolved into hexafluoroisopropanol to prepare a hexafluoroisopropanol solution with a polyglycolide concentration of 10% by weight and a hexafluoroisopropanol solution with a polylactide concentration of 10% by weight.

The rod-shaped body with the tubular porous body therearound was used as a collector electrode. The hexafluoroisopropanol solutions were discharged onto the surface of the rod-shaped body using an electrospinning device. At this time, the hexafluoroisopropanol solutions prepared above were charged into two different nozzles, and discharged while rotating the rod-shaped body and reciprocating the nozzles multiple times. Thus, an ultrafine fiber nonwoven fabric layer was formed.

The electrospinning was performed under the conditions of a voltage of −40 kV and a nozzle size of 23 G.

Finally, the rod-shaped body was pulled out to give a tubular artificial blood vessel with an external diameter of about 1,090 µm and an inner diameter of about 610 µm.

FIG. 1 shows electron micrographs of a cross section of the obtained tubular artificial blood vessel.

The tubular artificial blood vessel had a three-layer structure composed of a skin layer having a relatively small pore size (average pore size of 4.3 µm as measured in the same manner as in Experiment Example 1) as the innermost layer, a porous layer positioned around the skin layer and having a relatively large pore size (average pore size of 23.2 µm as measured in the same manner as the skin layer), and an ultrafine fiber nonwoven fabric layer on the porous layer.

(2) Evaluation of Blood Vessel Tissue Regeneration Performance

The artificial blood vessel obtained in Experiment Example 4 was evaluated by an animal test by the following method. Part of the abdominal aorta of mice was removed and replaced with the artificial blood vessel obtained in Experiment Example 4. Ten mice were tested. At the time of week 8 after the operation, all the ten mice were alive and no blood vessel blockage was observed at all.

Figure 2:
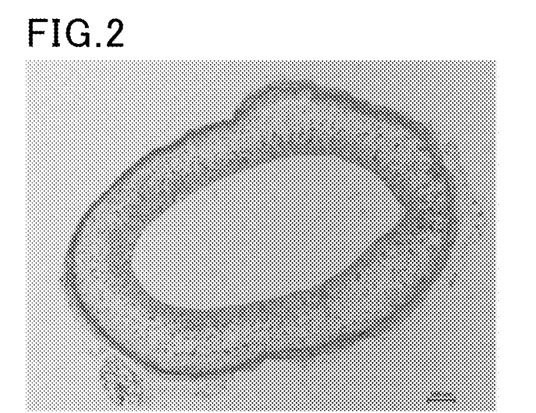
FIG. 2 shows an image of a blood vessel regenerated using the tubular artificial blood vessel obtained in Experiment Example 4, stained with HE.
Figure 3:
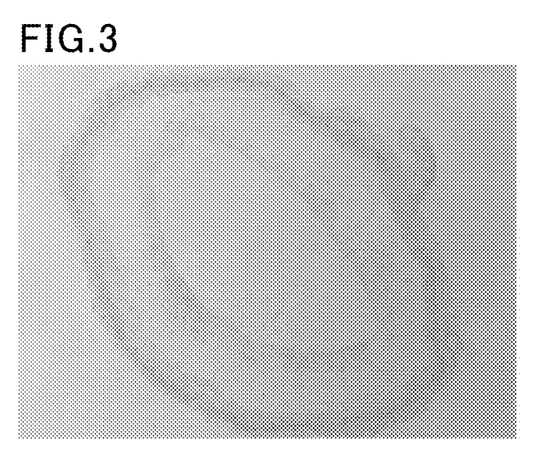
FIG. 3 shows an image of a blood vessel regenerated using the tubular artificial blood vessel obtained in Experiment Example 4, stained with von Kossa.

At week 8 after the operation, the mice were euthanized by intraperitoneal administration of excess pentobarbital, and the graft sites were harvested. FIG. 2 shows a micrograph image of one of the obtained specimens stained with hematoxylin-eosin (HE). FIG. 3 shows a micrograph image of one of the obtained specimens stained with von Kossa for calcification evaluation.

FIGS. 2 and 3 show regeneration of quite normal blood vessels without hypertrophy and calcification.

INDUSTRIAL APPLICABILITY

The present invention provides a method for producing a porous tissue regeneration substrate that allows a wide choice of solvents and easy adjustment of the bulk density and pore size of the porous substrate. The present invention also provides a method for producing an artificial blood vessel and an artificial blood vessel.

The invention claimed is:

1. A method for producing a porous, tubular artificial blood vessel containing a bioabsorbable material, the method comprising:
    a dissolving step of preparing a uniform solution containing a bioabsorbable polymer dissolved therein using a bioabsorbable polymer, a solvent 1 having a relatively low solvency for the bioabsorbable polymer, a solvent 2 having a relatively high solvency for the bioabsorbable polymer and being incompatible with the solvent 1, and a common solvent 3 compatible with the solvent 1 and the solvent 2;
    an applying step of applying the uniform solution to a surface of a rod-shaped body;
    a precipitating step of cooling the uniform solution on the surface of the rod-shaped body to precipitate a tubular porous body containing the bioabsorbable polymer around the rod-shaped body; and
    a freeze-drying step of freeze-drying the tubular porous body to give a tubular artificial blood vessel.

2. The method for producing an artificial blood vessel according to claim 1,
    wherein the rod-shaped body contains a metal.

3. The method for producing an artificial blood vessel according to claim 1, further comprising the step of discharging ultrafine fibers containing a bioabsorbable material on the surface of the tubular porous body by electrospinning to form an ultrafine fiber nonwoven fabric layer on the tubular porous body.

4. A method for producing a porous tissue regeneration substrate containing a bioabsorbable polymer, the method comprising:
    a dissolving step of preparing a uniform solution containing a bioabsorbable polymer dissolved therein using a bioabsorbable polymer, a solvent 1 having a relatively low solvency for the bioabsorbable polymer, a solvent 2 having a relatively high solvency for the bioabsorbable polymer and being incompatible with the solvent 1, and a common solvent 3 compatible with the solvent 1 and the solvent 2;
    a precipitating step of cooling the uniform solution to precipitate a porous body containing the bioabsorbable polymer; and
    a freeze-drying step of freeze-drying the porous body containing the bioabsorbable polymer to give a porous tissue regeneration substrate.

5. The method for producing a porous tissue regeneration substrate according to claim 4,
    wherein two or more common solvents 3 are used, and a pore size of the resulting porous body is controlled by adjusting a mixing ratio between the two or more common solvents 3.

* * * * *